United States Patent [19]
Weinberg

[11] Patent Number: 5,351,394
[45] Date of Patent: Oct. 4, 1994

[54] METHOD OF MAKING A NERVE ELECTRODE ARRAY

[75] Inventor: Steven L. Weinberg, League City, Tex.

[73] Assignee: Cyberonics, Inc., Webster, Tex.

[21] Appl. No.: 948,220

[22] Filed: Sep. 21, 1992

Related U.S. Application Data

[62] Division of Ser. No. 695,543, May 3, 1991, Pat. No. 5,251,634.

[51] Int. Cl.⁵ .............................................. H01R 43/00
[52] U.S. Cl. ........................................ 29/872; 29/825; 128/642
[58] Field of Search ............... 29/825, 857; 128/642, 128/784

[56] References Cited

U.S. PATENT DOCUMENTS

| | | | |
|---|---|---|---|
| 4,573,481 | 3/1986 | Bullana | 128/784 |
| 4,590,946 | 5/1986 | Loeb | 128/642 |
| 4,920,979 | 5/1990 | Bullana | 128/784 |
| 4,979,511 | 12/1990 | Terry, Jr. | 128/642 |
| 5,095,905 | 3/1992 | Klepinski | 128/642 |
| 5,215,089 | 6/1993 | Baker, Jr. | 128/642 |

OTHER PUBLICATIONS

IEEE Trans on Biomedical Engineering vol. 35, No. 11 Nov. 1988 pp. 905–915 by G. Naples et al.

*Primary Examiner*—Carl J. Arbes
*Attorney, Agent, or Firm*—O'Connor, Cavanagh, Anderson, Westover, Killingsworth, Beshears

[57] ABSTRACT

A method of making a nerve electrode is performed by forming an electrically insulative resilient array having an elongate backbone member with a plurality of spaced-apart substantially parallel bands, each spanning 360°, linked together by the backbone member and skewed from a direction normal to the backbone member; providing non-aligned single openings in the bands to render each of them incomplete with the remaining segments of each band linked by the backbone member and adapted to be spread apart to mount the array over the nerve and, when released, to resiliently close about the nerve; and securing an electrically conductive filament within at least one of the bands.

16 Claims, 2 Drawing Sheets

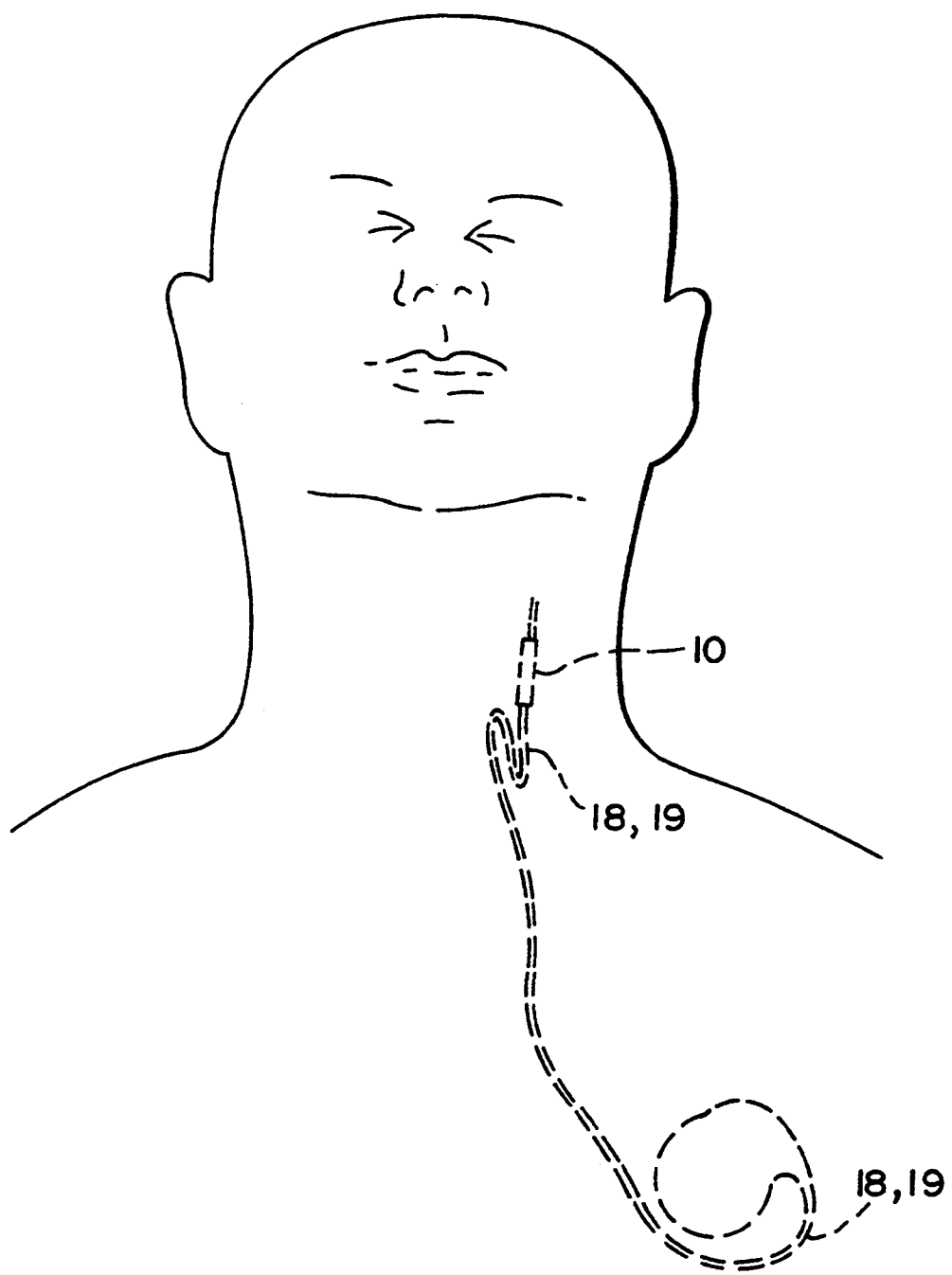

METHOD OF MAKING A NERVE ELECTRODE ARRAY

CROSS-REFERENCE TO RELATED APPLICATION

This application is a division of co-pending application Ser. No. 07/695,543 filed May 3, 1991 of the same inventor, now U.S. Pat. No. 5,251,634, issued Oct. 12, 1993.

BACKGROUND OF THE INVENTION

The present invention relates generally to nerve electrodes, and more particularly to a helical electrode which is implemented for ease of implantation on a nerve of the patient.

In U.S. Pat. No. 4,573,481, an implantable helical electrode assembly is disclosed in which the spiral configuration is composed of one or more flexible ribbon electrodes each partially embedded in a portion of the peripheral surface of a helically formed dielectric support matrix arranged and adapted to fit around a selected nerve or nerve bundle during surgical implantation of the electrode assembly. The resiliency of the assembly allows it to expand in the event of swelling of the nerve. The electrode assembly is utilized to electrically trigger or measure an action potential or to block conduction in nerve tissue.

Such a helical electrode provides a generally superior design for its intended purposes but has been found somewhat difficult to mount on the patient's nerve during implantation. In essence, to install it on the nerve requires that the helical configuration of the electrode assembly be unraveled and then reformed about the nerve.

SUMMARY OF THE INVENTION

According to the present invention, a helical configuration is employed for the electrode or electrode array, but the helix is locked together with a backbone which may be one-piece or divided into multiple segments. The electrode array is cut lengthwise through the entire helix at the side diametrically opposite to the backbone. The electrode array may then be spread at the cut ends of each loop, either one at a time or all together, and either manually or using an appropriate tool, to place it properly over the nerve and then allow the array to collapse, as a consequence of its resiliency, into its unrestrained normal spiral configuration about the nerve. This provides the desirable features of a conventional helical electrode array, but with an improved configuration which allows it be opened in a manner similar to a clamshell when desired to install it on or remove it from the nerve.

The principal advantages of the nerve electrode array of the present invention are its ease of installation and its elimination or at least reduction of serious trauma to the nerve both during and after implantation. In the latter respect, any subsequent swelling of the nerve is not restricted by the electrode. Some resistance to expansion may be experienced even with a closed helical electrode array of the type described in the aforementioned U.S. Pat. No. 4,573,481, because of the tendency of the central portion of such a helix to resist expansion as the helix is subjected to outwardly directed radial forces, notwithstanding that the end portions of the helix will readily deform to accommodate swelling of the nerve in their respective regions.

In an alternative preferred embodiment, the cut in each loop or band of the helix is staggered relative to the cuts in the other bands to assure that the electrode array does not slip or otherwise become displaced from the nerve in the usual event of swelling of the nerve following the surgical implantation. Such swelling is likely to occur after stabilization, in the first few days following implantation of the electrode array. Fibrotic growth occurs and tends to retain everything in place after the first week to ten days following the surgery.

A preferred method of making the nerve electrode array includes forming an electrically insulative helix having a plurality of spiral bands and a lengthwise or segmented partly lengthwise member further linking each of the bands together, securing an electrically conductive strip to the underside of one of the bands and across the linking member, and severing each of the bands at a point away from the linking member whereby each band remains linked to the member and may be spread open for mounting about the nerve. The severing of the bands, either in a line or in a staggered array relative to the linking member, lengthwise of the helix, is performed after the linking member is secured to the bands. As noted above, the linking member may be one piece or may be segmented as multiple pieces.

Accordingly, it is a broad object of the present invention to provide an improved helical nerve electrode array and method of making same.

Another object of the invention is to provide a helical electrode array which retains all of the desirable features of existing helical electrodes, while having the considerable advantage of ease of mounting on the selected nerve or nerve bundle.

A more specific object is to provide a helical nerve electrode assembly having spiral loops which may be opened independently of each other, or jointly, to allow ready placement of the electrode assembly over and about the nerve, and which has sufficient resiliency to collapse about and be retained around the nerve in its unrestrained spiral configuration.

A further object of the invention is to provide a method of making an improved helical electrode assembly, in which the assembly includes a plurality of spiral loops each of which is severed but remains in place by virtue of a backbone serving to link the loops together in the helical array configuration.

BRIEF DESCRIPTION OF THE DRAWINGS

The above and still further objects, features and attendant advantages of the invention will become apparent from a consideration of the following detailed description of certain preferred embodiments thereof, taken in conjunction with the accompanying drawings, in which:

FIG. 4 is a phantom view of a human patient, with a nerve electrode array of the invention mounted on the vagus nerve.

DETAILED DESCRIPTION OF THE PREFERRED EMBODIMENTS AND METHOD

Figure 1:
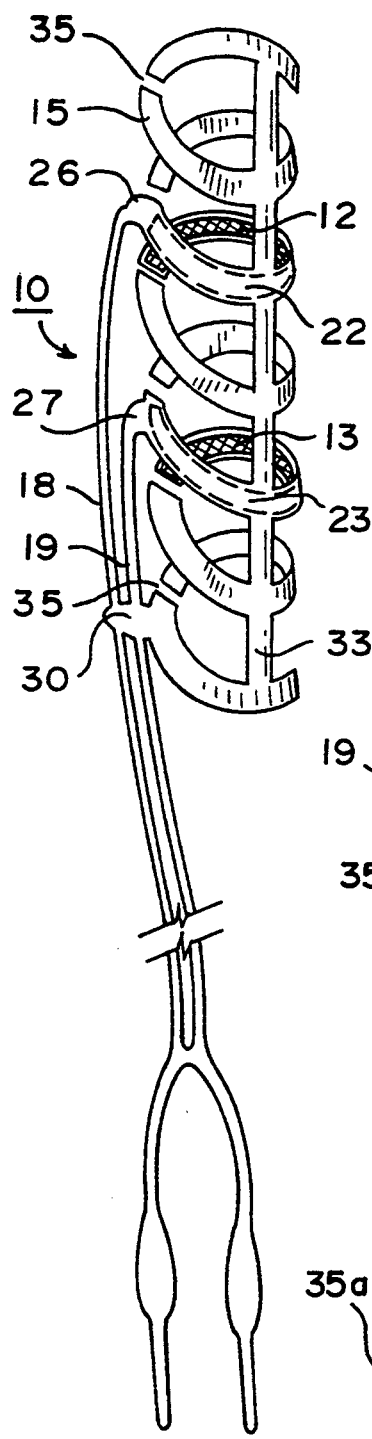
FIGS. 1, 2 and 3 are, respectively, a full perspective view and opposite side perspective views of a first preferred embodiment of a nerve electrode array according to the invention.
Figure 2:
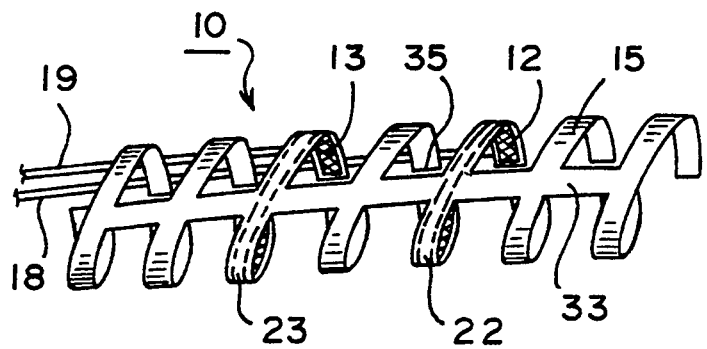
Figure 3:
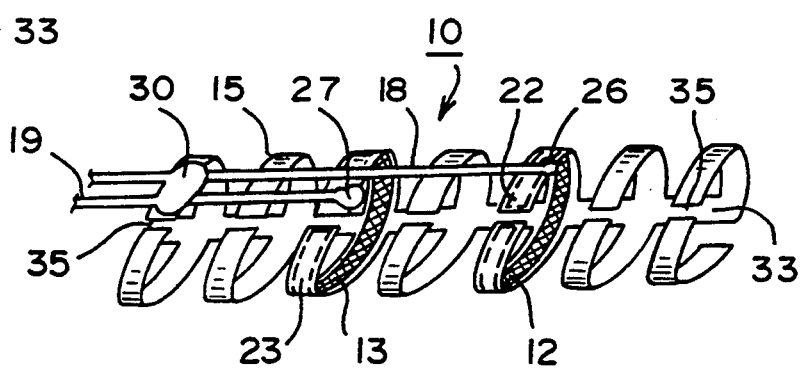

One presently preferred embodiment of a nerve electrode array 10 according to the invention is shown in FIGS. 1-3, inclusive. The electrode array 10 shown in the Figures is, by way of example and not limitation, bipolar (a unipolar array might alternatively be used), including a pair of electrically conductive ribbons, filaments or foils 12, 13 incorporated with and adhesively secured or bonded to an electrically insulative (nonconductive) spiral carrier 15. For example, the filaments 12, 13 may be composed of activated iridium, or rhodium or platinum, or other materials known to be suitable for the purpose, and the spiral or helical carrier 15 may be composed of medical grade silicone, such as those grades available from Dow Corning, or other known biocompatible material. The filaments are electrically attached to the distal or remote end of respective electrically conductive leads 18, 19, by welding or other known suitable technique.

The helix is formed preferably by casting the silicone over the electrodes, or alternatively by injection molding of the silicone over the electrodes, as they are held in a suitably shaped mold or die, so that each conductive filament is secured to the inside or underside of the helical assembly along only a portion of a respective band or coil 22, 23 of the helix 15, for reasons which will be apparent presently. During the molding process, an extra "bump" 26, 27 of silicone is formed at or near the point of attachment of the respective lead and its associated filament to strengthen the overall electrode 10 at each point of attachment. Each of the filaments and leads is covered with a respective insulative sheath of biocompatible material to minimize penetration of body fluids, and the leads may be further secured to an end of the helix by a tether 30, which may be simply another bump of silicone. The tether provides greater assurance that the leads will not be broken by the stresses that may be encountered during and after implant of the electrode, particularly at the respective points of attachment of the leads and electrodes. The proximal or near end of each lead is electrically attached to the appropriate terminals of an electrical connector designed to mate with the electrical connector of a generator (not shown) of electrical signals to be used for stimulation of the nerve and/or of a detector (not shown) for use in sensing the electrical signals carried by the nerve.

An important feature of the nerve electrode array 10 according to the present invention is that the helix 15 has each of its individual bands connected or linked by an electrically insulative spine or backbone 33 along its length at one side of the helix, and each of the conductive filaments, such as 12 and 13 in this embodiment, is approximately centered at or under this backbone. Preferably, the backbone is formed from silicone at the time of the casting of the helix about the filaments. After the device has been assembled to that stage, and allowed to cool, the helix 15 is cut lengthwise at the side opposite the backbone 33 so that each of its coils or bands is separable at the respective cut 35 therethrough, and the device is removed from the casting mold. The plural bands are held together by the backbone. Preferably, the cut 35 is through the silicone only (and not through the respective filament) in the bands containing the filaments. If, however, the filament is exposed at the cut, it may be insulatively sealed again on the edge surface of the helix by applying additional silicone to the cut end and allowing it to cure.

As a consequence of this construction, the electrode array 10 may be gently spread open as it is placed around the nerve during surgical implantation of the electrode on the selected nerve of the patient, such as the vagus nerve (FIG. 4). The resilience of the silicone spiral construction provides the helix with "memory" by which it tends to return to its normal spiral shape after the forces by which it is spread open are removed. After the nerve electrode has been installed in place, it is held in place by the coil segments of the silicone spiral not containing the conductive filaments as well as those coil segments which do contain the filaments.

Figure 5:
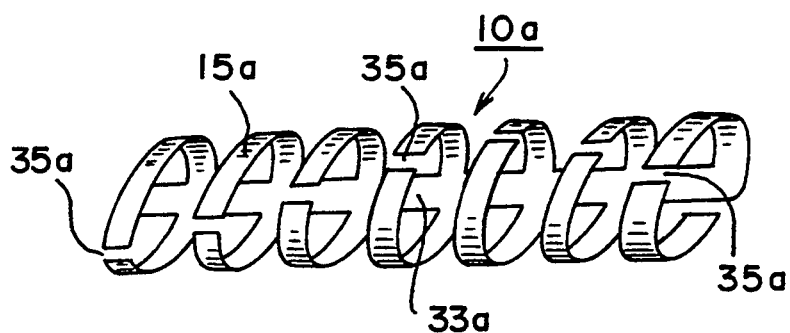
FIG. 5 is a side view of an alternative preferred embodiment of a nerve electrode array according to the invention.

In an alternative embodiment of the invention, shown in FIG. 5, the nerve electrode array 10a has non-aligned lengthwise cuts 35a in the individual bands of the helix 15a, making the cuts staggered relative to the backbone 33a. It should be apparent, both here and in the preferred embodiment of FIGS. 1-3 described above, that the cuts need not be oriented in a completely lengthwise direction (i.e., parallel to the axis), but instead may be slanted or skewed relative to that direction so long as they extend through the respective bands to allow the latter to be spread open for installation of the electrode on the nerve, as described above. In the embodiment of FIG. 5, however, the staggered cuts provide greater assurance that the helical nerve electrode array will not slip off or otherwise be displaced from the nerve in the event of swelling of the nerve or movement of the electrode with movements of the region of the body of the patient in which the electrode array is implanted.

It will thus be seen that the nerve electrode assembly constructed according to the principles of the present invention provides a superior configuration in that it retains the desirable electrical and mechanical features of the helical configuration, while being adapted for ease of mounting the assembly on the nerve itself, thereby significantly reducing the likelihood of trauma to the nerve during the installation.

Although certain presently preferred embodiments and methods of making such embodiments of the invention have been described herein, it will be apparent to those skilled in the relevant field to which the invention pertains from a consideration of the foregoing description, that variations and modifications of the disclosed embodiments and methods may be made without departing from the spirit and scope of the invention. It is therefore intended that the invention shall be limited only to the extent required by the appended claims and the rules and principles of applicable law.

What is claimed is:

1. A method of making a nerve electrode array, which comprises the steps of:
    forming an electrically insulative helix having a plurality of spiral bands, each spanning 360°, and a lengthwise member further linking the bands together,
    securing an electrically conductive filament in one of the bands for electrical connection to a lead wire at a site removed from the linking member, and
    severing each of the bands at a point away from the linking member whereby each band remains linked to the member and may be spread open for mounting the array about the nerve.

2. The method of claim 1, wherein:
    the electrically conductive filament is secured across the linking member in its band.

3. The method of claim 1, wherein:
the bands are severed in non-aligned breaks lengthwise of the helix.

4. The method of claim 1, wherein:
the bands are severed in a staggered array relative to the linking member, lengthwise of the helix.

5. The method of claim 1, including:
electrically connecting a lead wire to the filament at said site and tethering the wire to a band.

6. A method of making a nerve electrode, which comprises the steps of:
forming an electrically insulative resilient array having an elongate backbone member with a plurality of spaced-apart substantially parallel loops, each spanning 360°, linked together by the backbone member and skewed from a direction normal to the backbone member;
providing non-aligned single openings in the loops to render each of them incomplete with the remaining segments of each loop linked by the backbone member and adapted to be spread apart to mount the array over the nerve and, when released, to resiliently close about the nerve; and
securing an electrically conductive filament within at least one of the loops.

7. The method of claim 6, wherein:
the steps of forming and providing are performed in a single operation.

8. The method of claim 6, wherein:
the step of providing openings in the loops is performed by severing each complete loop lengthwise relative to the backbone member.

9. The method of claim 6, wherein:
the step of securing the electrically conductive filament is performed during the step of forming the array.

10. The method of claim 6, wherein:
the step of securing the electrically conductive filament is performed to position the filament across the linking member without crossing the opening in its loop.

11. The method of claim 6, wherein:
the step of providing openings in the loops is performed to place the opening in each loop at substantially the same location relative to the backbone member but skewed at an angle to the direction of the backbone member.

12. The method of claim 6, wherein:
the step of providing openings in the loops is performed to produce staggered openings relative to the backbone member, lengthwise of the array.

13. The method of claim 6, further including:
connecting an electrical lead to the filament at a point removed from the backbone member on the loop containing the filament.

14. The method of claim 13, further including:
tethering the electrical lead to a loop removed from the loop containing the filament.

15. The method of claim 6, wherein:
the step of forming the array is performed to produce spiral loops in a helical array.

16. The method of claim 6, wherein:
the step of forming the array is performed to produce substantially planar loops in a helix-like array.

* * * * *